(12) United States Patent
Wang

(10) Patent No.: US 7,956,100 B2
(45) Date of Patent: Jun. 7, 2011

(54) IMPLANTABLE MEDICAL DEVICES FABRICATED FROM BLOCK COPOLYMERS

(75) Inventor: Yunbing Wang, Sunnyvale, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 459 days.

(21) Appl. No.: 11/864,729

(22) Filed: Sep. 28, 2007

(65) Prior Publication Data

US 2009/0088835 A1 Apr. 2, 2009

(51) Int. Cl.
*A61F 2/06* (2006.01)
*C08G 63/08* (2006.01)
(52) U.S. Cl. ........................ 523/115; 528/354; 623/1.15
(58) Field of Classification Search .................. 523/115; 528/354; 623/1.15
See application file for complete search history.

(56) References Cited

U.S. PATENT DOCUMENTS

| | | | |
|---|---|---|---|
| 3,835,200 A | 9/1974 | Lee, Jr. | |
| 4,744,365 A | 5/1988 | Kaplan et al. | |
| 4,866,126 A | 9/1989 | Mylonakis et al. | |
| 5,716,981 A | 2/1998 | Hunter et al. | |
| 6,245,103 B1 * | 6/2001 | Stinson | 623/1.22 |
| 7,691,402 B2 * | 4/2010 | Guo et al. | 424/426 |
| 2001/0029398 A1 | 10/2001 | Jadhav | |
| 2004/0175406 A1 | 9/2004 | Schwarz | |
| 2004/0260386 A1 * | 12/2004 | Shalaby | 623/1.15 |
| 2006/0140999 A1 | 6/2006 | Lendlein et al. | |
| 2007/0224234 A1 | 9/2007 | Steckel et al. | |
| 2007/0231365 A1 | 10/2007 | Wang et al. | |
| 2007/0282426 A1 | 12/2007 | Wang et al. | |
| 2008/0033540 A1 | 2/2008 | Wang et al. | |
| 2008/0081063 A1 * | 4/2008 | Wang et al. | 424/426 |
| 2008/0107704 A1 * | 5/2008 | Guo | 424/423 |
| 2008/0147165 A1 * | 6/2008 | Hossainy et al. | 623/1.15 |
| 2008/0243228 A1 * | 10/2008 | Wang et al. | 623/1.15 |
| 2008/0247987 A1 * | 10/2008 | Liggins et al. | 424/78.17 |

FOREIGN PATENT DOCUMENTS

WO WO 2004/069097 8/2004
WO WO 2007/143116 12/2007

OTHER PUBLICATIONS

U.S. Appl. No. 11/51,271, filed Sep. 13, 2006, Wang et al.
U.S. Appl. No. 11/529,996, Sep. 29, 2006, Wang et al.
U.S. Appl. No. 11/729,173, filed Mar. 27, 2007, Wang et al.
U.S. Appl. No. 11/729,506, filed Mar. 28, 2007, Wang et al.
U.S. Appl. No. 11/784,925, filed Apr. 9, 2007, Wang et al.
U.S. Appl. No. 11/827,180, filed Jul. 10, 2007, Hossainy et al.
International Search Report for PCT/US2008/077477, mailed Feb. 11, 2010, 6 pgs.
U.S. Appl. No. 11/729,173, filed on Mar. 27, 2007, Wang et al.
Chen et al., "Preperation and characterization of biodegradable PLA polymeric blends", Biomaterials 24, pp. 1167-1173 (2003).
Ed. by Martuscelli et al., Polymer Blends "Processing, Morphology, and Properties", title pages and contents 6 pgs. (1979).
Kryszewski et al., "Recent progress in the studies on the preparation and properties of polymer blends. Polymer Blends: Processing, Morphology, and Properties", Plenum Press, N.Y. (1980).
Manli Zhang, et al., "The Effect Of Elastomeric Nano-Particles On The Mechanical Properties And Crystallization Behavior Of Polypropylene", Polymer 43, pp. 5133-5138 (2002).

* cited by examiner

*Primary Examiner* — Tae H Yoon
(74) *Attorney, Agent, or Firm* — Squire, Sanders & Dempsey (US) LLP

(57) ABSTRACT

Medical devices, such as stents, fabricated at least in part from a polymer composite including a biodegradable elastomeric phase dispersed within a biodegradable polymeric matrix are disclosed. The composite is composed of a block copolymer including an elastomeric homopolymer block and a glassy polymer block.

1 Claim, 8 Drawing Sheets

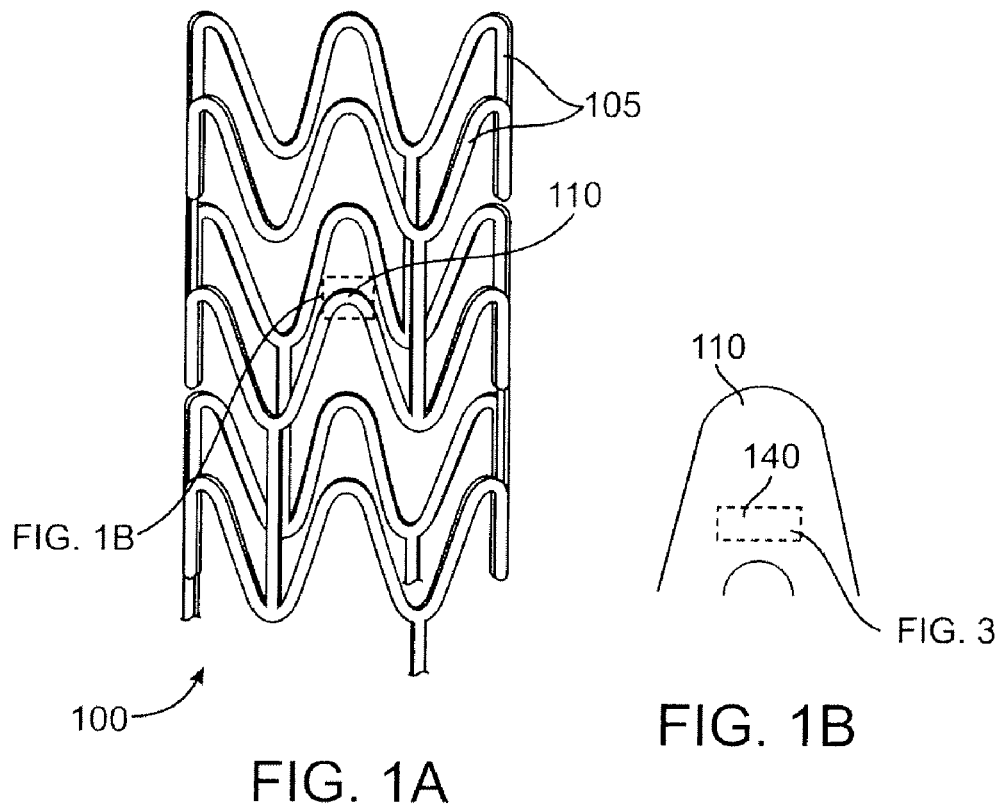
FIG. 1A
FIG. 1B
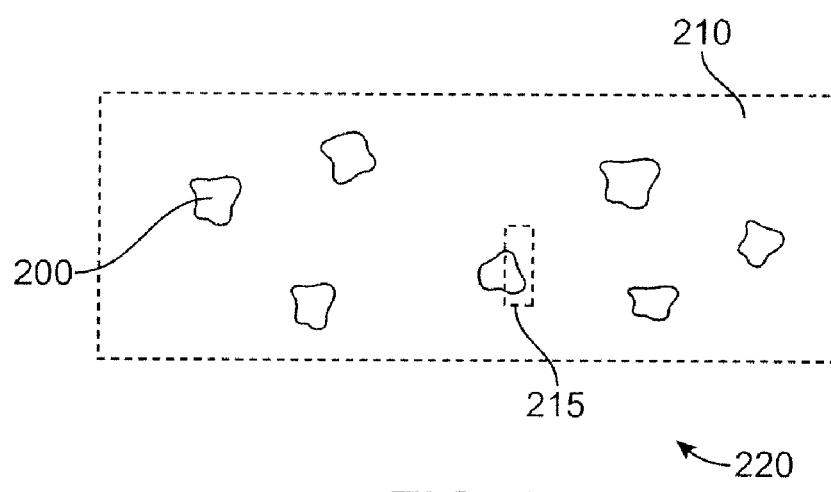
FIG. 3

IMPLANTABLE MEDICAL DEVICES FABRICATED FROM BLOCK COPOLYMERS

BACKGROUND OF THE INVENTION

1. Field of the Invention

This invention relates to implantable medical devices fabricated from polymer-polymer composites including block copolymers and methods of fabricating such implantable medical devices.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a constraining member such as a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil. In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodible materials such as bioabsorbable polymers should be configured to completely erode only after the clinical need for them has ended.

Potential problems with polymeric stents include that they may have inadequate toughness and they may have a degradation rate that is slower than is desirable for certain treatments.

SUMMARY OF THE INVENTION

Various embodiments of the present invention include a stent body fabricated at least in part from a polymer composite including a biodegradable elastomeric phase dispersed within a biodegradable polymeric matrix, the composite comprising: a block copolymer comprising an elastomeric homopolymer block and a glassy polymer block, wherein the elastomeric phase comprises the elastomeric homopolymer blocks and the matrix comprises the glassy blocks, wherein the elastomeric blocks are tougher than the glassy blocks and the polymeric matrix at physiological conditions.

Further embodiments of the present invention include a stent body fabricated at least in part from a polymer composite including an elastomeric phase dispersed within a matrix, the composite comprising: a block copolymer blended with a glassy matrix polymer, the block copolymer comprising an elastomeric homopolymer block and a glassy polymer block, the elastomeric phase comprising the elastomeric blocks and the matrix phase comprising the glassy matrix polymer and the glassy polymer blocks, wherein the elastomeric blocks are tougher than the glassy blocks and the glassy matrix polymer at physiological conditions.

Additional embodiments of the present invention include a stent body fabricated at least in part from a polymer composite including a biodegradable elastomeric phase dispersed within a polymeric matrix, the composite comprising: a block copolymer comprising an elastomeric homopolymer block and a glassy polymer block, wherein the elastomeric phase comprises the elastomeric homopolymer blocks and the matrix comprises the glassy blocks, the molecular weight of the glassy blocks being large enough to form the polymeric matrix, wherein the elastomeric blocks are tougher than the glassy blocks and the polymeric matrix at physiological conditions.

Other embodiments of the present invention include a stent body fabricated at least in part from a polymer composite including a biodegradable elastomeric phase dispersed within a polymeric matrix, the composite comprising: a block copolymer comprising an elastomeric polymer block and an PLGA block, wherein the elastomeric phase comprises the elastomeric blocks and the polymeric matrix comprises the PLGA blocks, the molecular weight of the PLGA blocks being large enough to form the polymeric matrix, wherein the elastomeric blocks are tougher than the glassy blocks and the polymeric matrix at physiological conditions.

BRIEF DESCRIPTION OF THE DRAWINGS

FIG. 1A depicts a stent.

FIG. 1B depicts a section of a structural element from the stent depicted in FIG. 1A.

FIG. 3 depicts a schematic close-up view of the section depicted in FIG. 1B.

DETAILED DESCRIPTION OF THE INVENTION

Figure 2:
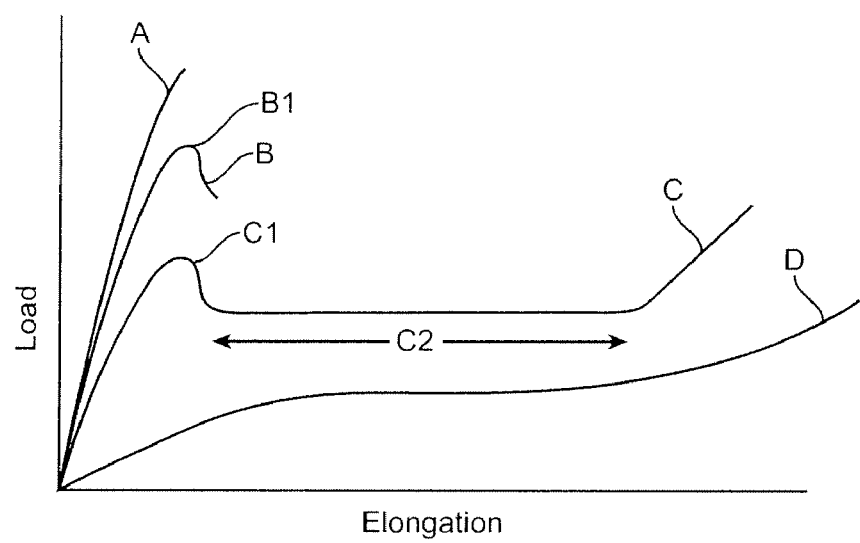
FIG. 2 represents the load-elongation curves for a typical polymer tested at four temperatures showing regions of mechanical behavior.

As used herein, an "implantable medical device" includes, but is not limited to, self-expandable stents, balloon-expandable stents, stent-grafts, and generally tubular medical devices.

An implantable medical device can be designed for the localized delivery of a therapeutic agent. A medicated implantable medical device may be constructed by coating the device or substrate with a coating material containing a therapeutic agent. The substrate of the device may also contain a therapeutic agent.

FIG. 1A depicts a view of a stent 100. In some embodiments, a stent may include a body or scaffolding having a pattern or network of interconnecting structural elements 105. Stent 100 may be formed from a tube (not shown). The pattern of structural elements 110 can take on a variety of patterns. The structural pattern of the device can be of virtually any design. The embodiments disclosed herein are not limited to stents or to the stent pattern illustrated in FIG. 1A. The embodiments are easily applicable to other patterns and other devices. The variations in the structure of patterns are virtually unlimited. A stent such as stent 100 may be fabricated from a tube by forming a pattern with a technique such as laser cutting or chemical etching.

An implantable medical device can be made partially or completely from a biodegradable, bioabsorbable, or biostable polymer. A polymer for use in fabricating an implantable medical device can be biostable, bioabsorbable, biodegradable or bioerodible. Biostable refers to polymers that are not biodegradable. The terms biodegradable, bioabsorbable, and bioerodible are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes.

Some polymers that may be suitable for implantable medical devices such as stents have potential shortcomings. For example, some crystalline or semi-crystalline polymers may be selected primarily on the basis of strength and stiffness at physiological conditions so that the stent substrate or scaffolding can provide adequate support for a lumen. Physiological conditions refer to conditions within a human patient including, but not limited to, body temperature. Such polymers may be glassy or have a Tg above body temperature making them stiff and strong at body temperature which is approximately 37° C. A "glassy polymer" refers to a polymer having Tg above body temperature. One such shortcoming of such crystalline or semi-crystalline polymers is that their toughness is lower than desired, in particular, for use in stent applications. For example, polymers such as poly(L-lactide) (PLLA), polyglycolide (PGA), or copolymers thereof, poly (L-Lactide-co-glycolide) (PLGA), tend to be brittle under physiological conditions or conditions within a human body.

PGA, relative to other biodegradable polymers, is highly crystalline, with a crystallinity range reported in the range of 35-75%. The molecular and subsequent crystalline structure of PGA allow very tight chain packing and consequently give to the material some very unique mechanical, physical, and chemical properties (See Table 1 below). For example, its specific gravity is around 1.5-1.7 which is very high for a polymeric material. It also has a high melting point and low solubility in most organic solvents. PGA, which is the simplest linear aliphatic polyester, degrades by hydrolysis of the easily accessible and hydrolytically unstable aliphatic-ester linkages. The degradation time, usually a few months, depends on multiple factors like molecular weight, degree of crystallinity, crystal morphology, and physico-chemical characteristics of the environment.

While structurally very similar to PGA, PLLA has some quite different chemical, mechanical and physical properties due to the presence of a pendant methyl group on the alpha carbon. This makes the PLA a chiral molecule and the D, L, and DL isomers are possible. PLLA are semicrystalline polymers, while D,L-PLA is a completely amorphous material. The methyl group in PLA makes the carbonyl of the ester link sterically less accessible to hydrolytic attack, which, depending on certain factors like the type of PLLA, its molecular weight, and its degree of crystallinity, makes the PLLA typically more hydrolytically stable than PGA when exposed to the same environment.

FIG. 2 represents the load-elongation curves for a typical polymer tested at four temperatures showing regions of mechanical behavior. Curve A is representative of a brittle fracture mechanism that occurs at low temperatures (below Tg). In curve A, the load rises approximately linearly with increasing elongation until a failure or a breaking point at the end of the curve. The elongation at the breaking point is typically less than 5%. In the behavior in curve A, there is little or no plastic deformation before failure. Curve B depicts a ductile fracture mechanism at higher temperatures in which a yield point B1 is observed after which the load falls before failure, typically between 10-20% elongation. Polymers exhibiting behavior shown in curves A and B can be very stiff (high modulus) and have a relatively high strength (load at failure). Such polymers have a relatively low toughness. Curve C represents the behavior of a polymer at still higher temperatures in which strain hardening occurs. After they yield point C1, the neck stabilizes and cold drawing ensues, as shown by flat region C2, with extensions up to 1000% often resulting. Curve D represents the behavior at even higher temperatures in which homogeneous, rubber-like deformation occurs, with a very large elongation at break. In an amorphous polymer, this rubber-like behavior occurs above the Tg, so the stress levels are very low.

As indicated below, one measure of toughness is the area under a stress-strain or load-elongation curve from zero strain to the strain at fracture. Therefore, the modulus, stress at fracture (strength), and elongation at fracture are relevant to the toughness of a polymer. For example, a polymer with a lower strength can have a higher toughness than a brittle polymer if it has a higher elongation at break and a lower modulus.

One way to increase fracture toughness of a low fracture toughness polymer under physiological conditions is to form a polymer-polymer composite that includes the low fracture toughness polymer blended with a polymer having a higher fracture toughness at physiological conditions. A "composite" refers generally to a material in which two or more distinct, structurally complementary substances combine to produce structural or functional properties not present in any individual components. The two or more distinct substances may be combinations of different classes of materials such as metals, ceramics, glasses, and polymers. The two or more substances can also be a combination of two or more different polymers that form different phases.

In such a polymer-polymer composite, the low fracture toughness polymer is blended with another polymer having a higher or relatively high fracture toughness under physiological conditions. The higher fracture toughness polymer is also immiscible and forms a discrete or dispersed phase within the low fracture toughness polymer. The discrete phase can absorb energy arising from stress imparted to a device made from the composite to increase the fracture toughness of the device. To ensure good energy transfer between interfaces of the phases, it is important that there be sufficient bonding or adhesion between the phases. See, Y. Wang, etc. Journal of Polymer Science Part A: Polymer Chemistry, 39, 2001, 2755-2766.

Another shortcoming of some biodegradable polymers is their degradation rate can be slower or faster than desired for certain stent treatments. For instance, the degradation rate may be too slow. As a result, the degradation time of a stent made from such a polymer can be longer than desired. Reducing degradation time allows further surgery or intervention, if necessary, on a treated vessel to occur sooner. Additionally decreasing degradation time helps cut down on the cases of late stent thrombosis, a condition in which clots form on the surface of the stent months or years after deployment. For example, a stent made from PLLA can have a degradation time of between about two and three years or longer (See Table 1). "Degradation time" refers to the time for a stent implanted in a vessel to completely absorb. "Degradation time" can also refer to the time for a stent to completely absorb under in vitro conditions. In some treatment situations, a degradation time of less than a year may be desirable, for example, between three and 12 months, or more narrowly, between four and eight months.

The degradation of a hydrolytically degradable polymer follows a sequence including water penetration into the polymer followed by hydrolysis of bonds in the polymer. Thus, the degradation of a polymer can be influenced by its affinity for water and the diffusion rate of water through the polymer. A hydrophobic polymer has a low affinity for water which results in a relatively low water penetration. In addition, the diffusion rate of water through crystalline regions of a polymer is lower than amorphous regions. Thus, as either the affinity of a polymer for water decreases or the crystallinity increases, water penetration and water content of a polymer decreases, resulting in a slower degradation rate.

Various embodiments of the present invention include an implantable medical device, such as a stent, fabricated at least in part of a polymer-polymer composite including a discrete polymer phase dispersed within a polymer matrix or continuous polymer phase. In some embodiments, the discrete phase polymer has a higher toughness than the matrix polymer. In such embodiments, the higher toughness polymer can have a higher elongation at break, a lower modulus, or both. In other embodiments, the discrete phase polymer has a higher degradation rate than the matrix polymer. In some embodiments, the discrete phase increases the toughness of the composite, increases the degradation rate of the composite, or increases both the toughness and degradation rate of the composite.

In exemplary embodiments, the higher toughness polymer can have an elongation at break at least 2, 4, 10, or at least 100 times greater or greater than 100 times greater than the polymer matrix. In other exemplary embodiments, the higher toughness polymer can have a modulus less than 20%, 50%, or less than 80% of the matrix polymer. In some exemplary embodiments, the degradation time of the higher toughness polymer can be less than 20%, 30%, 50%, or less than 80% of the degradation time of the matrix polymer.

FIG. 1B depicts a section of a segment 110 of strut 105 from the stent depicted in FIG. 1A. FIG. 3 depicts a microscopic section 220 of a portion 140 of segment 110 of the strut as depicted in FIG. 1B. Portion 140 includes a discrete or dispersed phase 200 within a continuous phase 210.

Generally, a polymer-polymer or polymer blend exhibits properties that can markedly vary from those of the individual polymers. Macaúbas P. H., Demarquette N. R., Rheology as a Tool for Immiscible Polymer Blends Characterization: Interfacial tension and compatibilization, in RheoFuture. 2002, Thermo Electron Corporation: Karlsruhe, Germany. The higher fracture toughness polymer can enhance the fracture toughness of the composite. It is believed that when a device is placed under stress, the discrete phase tends to absorb energy when a fracture starts to propagate through a structural element. Crack propagation through the continuous phase may then be reduced or inhibited. As a result, fracture toughness of the composite, and thus structural elements of a device fabricated from the composite is increased. Thus, brittle polymers can be toughened by incorporating into their microstructure higher toughness components that can act as "stress concentrators", due to their lower tensile modulus. The embedded stress concentrators in the more brittle continuous phase permit elastic energy storage or ductile yield mechanisms that increase its resistance to fracture. Meredith J. C., Amis E. J., LCST phase separation in biodegradable polymer blends: poly(D,L-lactide) and poly(ε-caprolactone), Macromol. Chem. Phys., 2000. 201(6): p. 733-739.

In certain embodiments, the discrete phase polymer is elastomeric. An "elastomeric" or "rubbery" polymer refers to a polymer which can resist and recover from deformation produced by force, as in natural rubber. In one embodiment, elastomers or rubbery polymers can be stretched repeatedly to at least twice their original length and, immediately upon release of the stress, return with force to their approximate original length. Elastomeric polymers tend to have a percent elongation at break larger than lower toughness polymers, such as brittle polymers.

In some embodiments, the low toughness polymer can be above its Tg. In some embodiments, the low toughness polymer, such as an elastomeric polymer, of the dispersed phase has a Tg below body temperature. In other embodiments, the low toughness polymer of the dispersed phase has a Tg below ambient temperature. Ambient temperature can refer to a temperature between 20° C. and 30° C. Additionally, some elastomers or rubbery polymers are substantially or completely amorphous.

Certain embodiments of the present invention include a stent body fabricated at least in part from a polymer-polymer composite including a block copolymer that includes a glassy polymer block and a block with a higher toughness than the glassy polymer block. In some embodiments, the high toughness block is an elastomeric block. The embodiments described below refer to an elastomeric block. In such embodiments, generally, a block having a toughness higher than the glassy block can be used. In these embodiments, the discrete phase includes the elastomeric blocks and the matrix or continuous phase includes the glassy blocks. The embodiments of the higher toughness polymer with respect to the toughness, strength, modulus, and elongation at break correspond to the high toughness block or elastomeric block.

Various embodiments of the block copolymer within the composite are contemplated. In a first set of embodiments, the composite can be a blend of the block copolymer and a matrix polymer. In such embodiments, the discrete phase includes the elastomeric blocks and the continuous phase includes the glassy blocks and the matrix polymer. In a second set of embodiments, the composite can be a blend of the block copolymer, an elastomeric polymer, and a matrix polymer. In such embodiments, the discrete phase includes the elastomeric polymer and the elastomeric blocks and the continuous phase includes the glassy blocks and the matrix polymer. In a third set of embodiments, the composite can include a block copolymer having glassy blocks with molecular weights high enough such that the glassy blocks make up a substantial portion or up to 100% of the matrix or continuous phase.

In all such embodiments, one or more structural elements or struts of a stent can be fabricated from the composite. In other such embodiments, the body, scaffolding, or substrate of a stent can be made from the composite. The body, scaffolding, or substrate may be primarily responsible for providing mechanical support to walls of a bodily lumen once the stent is deployed within the bodily lumen. A stent body, scaffolding, or substrate can refer to a stent structure with an outer surface to which no coating or layer of material different from that of which the structure is manufactured. If the body is manufactured by a coating process, the stent body can refer to a state prior to application of additional coating layers of different material. By "outer surface" is meant any surface however spatially oriented that is in contact with bodily tissue or fluids. A stent body, scaffolding, or substrate can refer to a stent structure formed by laser cutting a pattern into a tube or a sheet that has been rolled into a cylindrical shape.

In some embodiments, a majority, substantially all, or all of the stent body, scaffolding, or substrate can be made from the composite. Substantially all of the body can refer to greater than 90%, 95%, or greater than 99% of the body.

Generally, it is desirable for the discrete phase regions to be uniformly or substantially uniformly dispersed throughout the continuous polymer phase to facilitate the increase in toughness. The more dispersed the discrete phase regions, the greater is the increase in toughness. Additionally, the increase in toughness is related to the size of the discrete phase. Both the degree of dispersion and discrete phase size can be controlled by the length or molecular weight of the elastomeric blocks. The characteristic length of a discrete phase can be 1 nm to 100 nm, 100 nm to 500 nm, 500 nm to 1,000 nm, 1000 nm to 10,000 nm, or greater than 10,000 nm. In some embodiments, the molecular weight of the elastomeric blocks can be between about 1 kg/mol to 50 kg/mol to obtain a desired characteristic length of the discrete phase regions. In other embodiments, the molecular weight of the elastomeric blocks can be 50-100 kg/mol, 100-150 kg/mol, or greater than 150 kg/mol.

In the first and second set of embodiments, the primary purpose of the glassy blocks is to facilitate adhesion between the discrete phase and the continuous phase. Thus, the length of the glassy blocks is relatively small or short compared to the matrix polymer chains. It follows that the molecular weight of the glassy blocks is relatively small compared to the molecular weight of the matrix polymer. In such embodiments, the molecular weight of the glassy blocks can be 20-200 kg/mol or greater then 200 kg/mol.

In the first set of embodiments, the composite of the stent body includes a blend of the block copolymer and a matrix polymer. In such embodiments, the discrete phase includes the elastomeric block and the continuous phase includes the glassy matrix polymer. In some embodiments, the matrix polymer is a majority of the polymer blend, where majority means greater than 50 wt %. In further embodiments, the matrix polymer is greater than 60, 80, 95, or greater than 99 wt % of the polymer blend. In these embodiments, the elastomeric block is immiscible with the matrix polymer, allowing for the formation of the discrete phase dispersed within the matrix polymer. The elastomeric blocks of the discrete phase tend to increase the toughness of the matrix polymer, and thus the composite.

Figure 4:
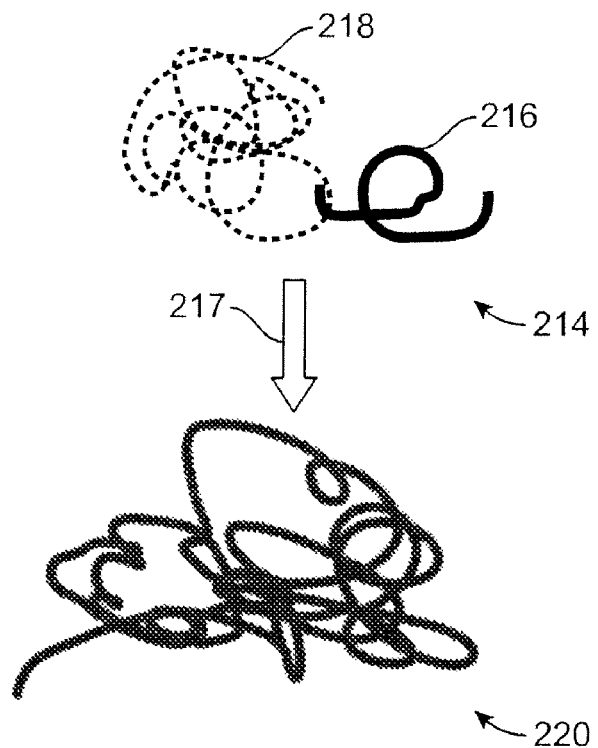
FIG. 4 depicts a schematic illustration of formation of a binary polymer blend.

FIG. 4 depicts a schematic illustration of formation of a binary blend of a block copolymer and a matrix polymer. A block copolymer 214 includes an elastomeric block 218 and a glassy block 216. Block copolymer 214 is blended with a matrix polymer 220, as shown by an arrow 217.

Furthermore, in some embodiments, the glassy blocks are miscible with the matrix polymer to allow the glassy blocks to partially or completely phase separate into the continuous phase so that the glassy blocks are within the continuous phase. In such embodiments, the chemical composition of the glassy blocks is the same as the matrix polymer. In these embodiments, the glassy blocks act as anchor segments that tend to increase the adhesion between the discrete phase and the continuous phase by binding the phases together. Thus, the glassy blocks facilitate energy transfer between interfaces of the phases, allowing the discrete high toughness phase to increase the toughness of the composite. It is expected that the increase in toughness of the composite depends on the degree of adhesion between the continuous and discrete phases.

Figure 5:
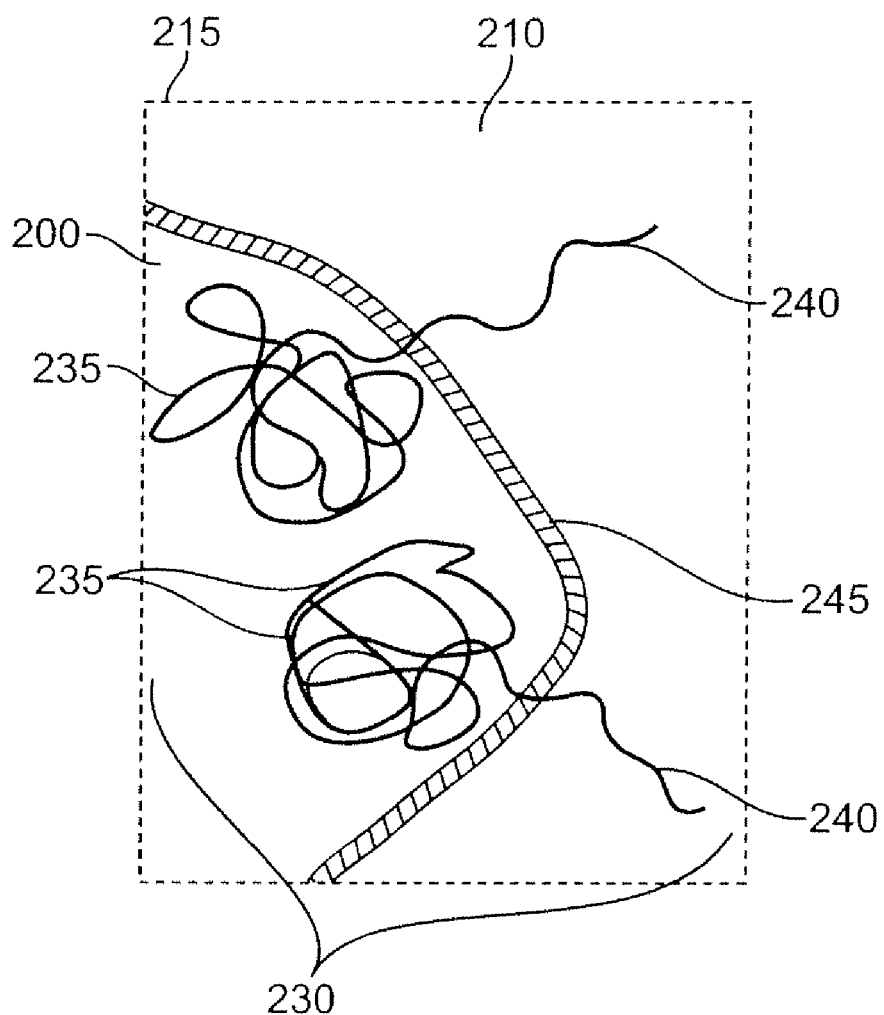
FIG. 5 depicts a schematic close-up view of an interface between a discrete polymer phase and a continuous polymer phase.

FIG. 5 depicts a schematic close-up view of section 215 including an interface between discrete phase 200 and continuous polymer phase 210. A block copolymer 230 includes elastomeric blocks 235 and glassy blocks 240. Line 245 is meant to delineate the boundary between discrete phase 200 and continuous phase 210. Glassy blocks 240 are shown to be within continuous phase 210.

Additionally, the degree of adhesion depends upon the molecular weight of the glassy blocks. It is expected that as the molecular weight of the glassy blocks increases, the degree of adhesion between the discrete and continuous phases increases. Thus, in some embodiments, the molecular weight of the glassy blocks can be adjusted to be high enough to allow the discrete phase to increase the toughness of the composite. As indicated, above, the glassy blocks can be the same or similar composition as the matrix polymer. The molecular weight of the glassy blocks can be up to 10%, 20%, 30%, or up to 40% of the molecular weight of the matrix polymer.

In general, the elastomeric blocks of the block copolymer are selected that have a higher fracture toughness than the matrix polymer. In some embodiments, as discussed above, the elastomeric blocks can have a lower modulus, higher elongation at break, or both than the matrix polymer. In certain embodiments, the elastomeric blocks can be include functional units or groups that form high fracture toughness or elastomeric polymers. Biodegradable polymers having a relatively high fracture toughness include, but are not limited to, polycaprolactone (PCL) and poly(trimethylene carbonate) (PTMC), polydioxanone (PDO), poly(4-hydroxy butyrate) (PHB), and poly(butylene succinate) (PBS). Thus, some embodiments of elastomeric blocks can include CL, TMC, DO, HB, and BS monomers. The mechanical and degradation properties of some of these polymers are provided in Table 1.

Furthermore, a matrix polymer, such as PLLA, PGA, or PLGA, can have a degradation rate that is slower than desired for certain stent treatments. In certain embodiments, the elastomeric blocks can be selected so that the discrete phase increases the degradation rate of the composite. The discrete phase can include a polymer that has a higher degradation rate than the matrix polymer. In such embodiments, the discrete phase can decrease the degradation time of a composite stent or a portion of a stent fabricated from the composite. In some embodiments, the degradation time of a composite stent can be less than 75%, 50%, 40%, or less than 25% of a stent fabricated from the matrix polymer.

In exemplary embodiments, the elastomeric blocks can be selected to increase the toughness of a composite for a device. Additionally, the elastomeric blocks can be selected to increase or decrease the degradation rate or time of a device fabricated from the composite. Table 1 shows PCL and PDO polymers that have a lower modulus and larger elongation at break than PLLA, PGA, and PLGA. PCL is an elastomeric polymer with a relatively lower modulus and an elongation at break many times larger than PLLA, PGA, and PLGA. However, the degradation rate is similar to PLLA. Thus, an elastomeric block containing CL is expected to increase the toughness, as shown by the higher elongation at break and lower modulus, but may not increase the degradation rate of a composite. PDO also has a lower modulus than PLLA, PGA, and PLGA, however, it elongation at break, although higher than these polymers, is much lower than PCL. However, PDO has a higher degradation rate than PCL. As result, an elastomeric block including DO is expected to increase the degradation rate of the composite and decrease the degradation time of a composite made from the composite. As discussed below, the elastomeric block can be a copolymer or homopolymer.

TABLE 1

Properties of biodegradable polymers.

| Polymer | Melting Point (° C.)[1] | Glass-Transition Temp (° C.)[1] | Modulus (Gpa) | Tensile Strength (Mpa) | Elongation at break (%) | Degradation Time (months)[a] |
|---|---|---|---|---|---|---|
| PGA | 225-230[1] | 35-40 | 7.0[1] 5-7[2] | 60-80[2] | 30[4] | 6-12[1,2] |
| PLLA | 173-178[1] | 60-65 | 2.7[1] 3[2] | 60-70[2] | 3[4] | >24[1] >36[2] |
| PDLLA | Amorphous | 55-60 | 1.9[1] 2[2] | 2[2] | N/A | 12-16[1] 12-15[2] |
| PCL | 58-63[1] 60[4] | (−65)-(−60) | 0.4[1,2] 0.386[4] | 20-25[2] 4[4] | 800-1000[4] | >24[1] >36[2] |
| PDO | N/A | (−10)-0 | 1.5[1,2] | 30[2] | 35[3] | 6-12[1] 6[2] |
| PHB | 177[4] | N/A | 4[4] | 40[4] | 6[4] | |
| PGA-TMC | N/A | N/A | 2.4[1] | N/A | N/A | 6-12[1] |
| 85/15 PLGA | Amorphous | 50-55[1] | 2.0[1] | N/A | N/A | 5-6[1] |
| 75/25 PLGA | Amorphous | 50-55[1] | 2.0[1] | N/A | N/A | 4-5[1] |
| 65/35 PLGA | Amorphous | 45-50[1] | 2.0[1] | N/A | N/A | 3-4[1] |
| 50/50 PLGA | Amorphous | 45-50[1] | 2.0[1] | N/A | N/A | 1-2[1] |

[1] Medical Plastics and Biomaterials Magazine, March 1998.
[2] Medical Device Manufacturing & Technology 2005.
[3] The Biomedical Engineering Handbook, Joseph D. Bronzino, Ed. CRC Press in Cooperation with IEEE Press, Boca Raton, FL, 1995.
[4] Science, Vol. 297 p. 803 (2002)
[a] Degradation time also depends on part geometry.

Furthermore, the toughness and degradation rate of the composite depend upon the content (e.g., weight percent) of block copolymer. The toughness and degradation rate are expected to increase as the content of the block copolymer increases. However, as the content increases, the flexibility of the composite is also expected to increase, with a simultaneous decrease in radial strength. Thus, the content of the block copolymer can become so high that the radial strength of the composite can be too low for a stent scaffolding.

In some embodiments, the elastomeric block can be a copolymer. One advantage of a copolymer over a homopolymer elastomeric block is that the presence of more than one functional group reduces crystallinity, which increases the degradation rate of the discrete phase. Thus, the degradation rate of the copolymer may be a degradation rate that is higher than the matrix polymer, which can decrease the degradation time of the composite. Another advantage of a copolymer is that the presence of more than one functional group allows an additional degree of freedom to tune the toughness or degradation rate of the discrete phase. Both the properties (mechanical properties, degradation rate or time) and the relative composition of a functional group can influence the properties of the composite.

As an example, Table 1 shows, a homopolymer elastomeric block including CL may increase the toughness of a composite, but may not be capable to increasing the degradation rate a desired degree. Thus, the copolymer can include a functional group that enhances the toughness (high toughness functional group) and a functional group that increases the degradation rate (a fast degrading functional group). In particular, the elastomeric block can include a fast degrading monomer that has a higher affinity for water and/or is more hydrolytically active than the high toughness functional group or the matrix polymer.

In an exemplary embodiment, the elastomeric block can include glycolide (GA) monomers which are faster degrading than a high toughness functional group, such as CL or TMC, and the matrix polymer, such as PLLA. Exemplary elastomeric blocks can be P(GA-co-CL) or P(GA-co-TMC) random or alternating copolymer. The faster degrading GA monomers can increase the degradation rate of the polymer composite by increasing the equilibrium water content and penetration into the composite. Acidic and hydrophilic degradation products of the GA segments also act to increase the degradation rate of the composite.

In some embodiments, the toughness and degradation rate of the discrete phase can be adjusted by the ratio of fast degrading and high toughness functional groups. As the ratio of CL, for example, increases in P(GA-co-CL) segments, the polymer becomes more flexible and tougher. Also, the Tg of the discrete phase segments can be tuned to a desired value by adjusting the ratio of component monomers. For example, the Tg of the discrete phase may be engineered to be less than a body temperature to provide a more flexible discrete phase under physiological conditions. Additionally, the degradation rate of the discrete phase, and thus the blend, can be increased by increasing the fraction of GA in the discrete phase segments. In exemplary embodiments, the P(GA-co-CL) segments can have greater than 1 wt %, 5 wt %, 20 wt %, 50 wt %, 70 wt %, 80 wt %, or 90 wt % GA monomer.

Exemplary block copolymers include P(GA-co-CL)-b-PLLA and P(GA-co-TMC)-b-PLLA. In a binary polymer blend of the block copolymer of P(GA-co-CL)-b-PLLA with a matrix polymer of PLLA, the PLLA block phase separates into the PLLA matrix of the continuous phase. The PLLA block binds the discrete phase to the continuous phase, facilitating the increase in the fracture toughness of the polymer blend. In exemplary embodiments, the polymer blend or composite can include about 1-40 wt %, or more narrowly 5-30 wt % of a block polymer and about 75-95 wt % of matrix polymer.

In other embodiments, the elastomeric block can be a homopolymer. An advantage of a homopolymer elastomeric block over a copolymer is that the synthetic process is simplified, as described below. The homopolymer can be selected to provide a desired toughness (mechanical properties) and degradation rate for the composite. In an exemplary embodiment, the elastomeric block can be a homopolymer of PCL, PDO, PHB, or PBS. The toughness and degradation rate can be tuned by the weight percent of the elastomeric blocks in the composite. Exemplary block copolymers can include PCL-b-PLLA, PDO-b-PLLA, PHB-b-PLLA, or PBS-b-PLLA. In exemplary embodiments, the polymer blend or composite can include about 1-40 wt %, 5-25 wt %, or more narrowly 5-30 wt % of one of the above exemplary block copolymers in PLLA.

As shown in Table 1, the PDO block has a much shorter degradation time than the PLLA, the PDO block can degrade within one year. Also, the degradation products of PDO and other elastomeric blocks are acidic and hydrophilic. Thus, as the PDO and these other elastomeric blocks erode, they will form acidic degradation products that will serve to enhance the degradation rate of PLLA. The degradation products are also hydrophilic, which will serve to increase the equilibrium level of moisture in the polymer. Both of these mechanisms will increase the degradation rate of any implants manufactured from these materials. In addition, as elastomeric blocks of the block copolymer erode, they will leave a porous structure behind, which serves to enhance the degradation rate of the PLLA.

In exemplary embodiments, the LLA content of the PLLA block of the above-mentioned block copolymers is less than 20 wt %, 30 wt %, 50 wt %, or greater than 50 wt % of the block copolymer. In other exemplary embodiments, the molecular weight of the PLLA block is less than 50 kg/mol, 60 kg/mol, 70 kg/mol, or greater 70 kg/mol.

The composite can be formed by mixing or blending the block copolymer with a matrix polymer. The polymers can be blended using various mixing methods know in the art, for example, by mixing the polymer in an extruder. Representative examples of extruders include, but are not limited to, single screw extruders, intermeshing co-rotating and counter-rotating twin-screw extruders and other multiple screw masticating extruders.

In the second set of embodiments, the composite can be a blend of the block copolymer, an elastomeric polymer, and a matrix polymer. In these embodiments, the elastomeric copolymer makes up a majority of or a substantial portion of the discrete phase. In exemplary embodiments, the elastomeric polymer is greater than 50, 60, 80, 95, or greater than 99 wt % of the discrete phase. The elastomeric polymer can be the same as the elastomeric blocks of the block copolymer. Alternatively the elastomeric polymer can have a slightly different composition as long the elastomeric polymer and the elastomeric blocks are miscible.

Figure 6:
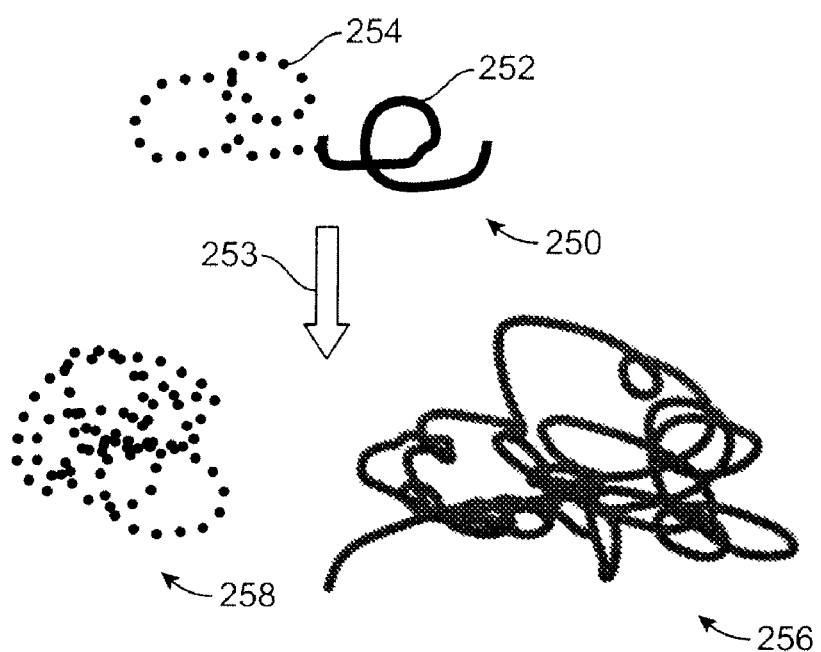
FIG. 6 depicts a schematic illustration of formation of a ternary polymer blend.

FIG. 6 depicts a schematic illustration of formation of a ternary blend of a block copolymer, an elastomeric polymer, and a matrix polymer. A block copolymer 250 includes an elastomeric block 254 and a glassy block 252. The ternary blend also includes an elastomeric polymer 258 and a matrix polymer 256. Block copolymer 250 is blended with elastomeric polymer 258 and matrix polymer 256, as shown by an arrow 253.

In these embodiments, the elastomeric polymer can be random or alternating copolymer. The elastomeric polymer can have a composition as described above for the elastomeric blocks. In some embodiments, the molecular weight of the elastomeric blocks can be between about 1 kg/mol to 50 kg/mol. In other embodiments, the molecular weight of the elastomeric blocks can be 50-100 kg/mol, 100-150 kg/mol, or greater than 150 kg/mol.

In exemplary embodiments, the elastomeric polymer can be, for example, P(CL-co-GA) and P(TMC-co-GA). The elastomeric polymer can also be a homopolymer. Exemplary elastomeric homopolymers include, for example, PDO, PCL, PTMC and PHB.

In these embodiments, the block copolymer tends to act as a compatibilizer between the matrix polymer and the elastomeric polymer by facilitating adhesion between the discrete and continuous phases. In general, a "compatibilizer" refers to an interfacial agent that modifies the properties of an immiscible polymer blend which facilitates formation of a uniform blend, and increases interfacial adhesion between the phases. Compatibilization refers to the process of modification of the interfacial properties in an immiscible polymer blend that results in formation of an interphase (region of concentration gradient between phases) and stabilization of the morphology.

One advantage of the ternary composite is that the degree of adhesion between the discrete and continuous phases is at least partially decoupled from the adjustment of the toughness and degradation rate of the composite. The degree of adhesion depends on the weight percent, composition, and molecular weight of the block copolymer. Although the block copolymer influences the mechanical properties and degradation rate, the properties of the elastomeric polymer likely have a greater influence on the mechanical properties of the composite since the elastomeric polymer makes up most of the discrete phase.

In an exemplary embodiment, a ternary blend can include PLLA as the matrix polymer; PDO, PCL, PTMC, PHB, or PBS as the elastomeric polymer; and PDO-b-PLLA or PCL-b-PLLA, PCL-b-PLLA, PTMC-b-PLLA, PHB-b-PLLA or PBS-b-PLLA as the block copolymer. In such embodiments, one or the above-mentioned elastomers is in the discrete phase along with the elastomeric blocks of the block polymer. The PLLA blocks phase separate into the PLLA matrix polymer of the continuous phase. In exemplary embodiments, a ternary polymer blend can include about 1-40 wt %, or more narrowly, 5-30 wt % of the elastomeric polymer; and about 0.5-5% wt % of the block copolymer.

The composite can be formed by mixing or blending the block copolymer with the elastomeric polymer and matrix polymer. In an exemplary embodiment, a ternary blend can include PLLA as the matrix polymer; P(GA-co-CL) copolymer; and P(GA-co-CL)-b-PLLA. In such embodiments, P(GA-co-CL) copolymer is in the discrete phase along with P(GA-co-CL) blocks of the block polymer. The PLLA blocks phase separate into the PLLA matrix polymer of the continuous phase. In exemplary embodiments, a ternary polymer blend can include about 1-40 wt %, or more narrowly, 5-30 wt % of a P(GA-co-CL); and about 0.5-5% wt % of P(GA-co-CL)-b-PLLA.

In further embodiments, the matrix polymer can be a copolymer with functional groups selected to increase the degradation rate of the matrix polymer. Such a functional group can have a greater affinity for water or be more hydrolytically active than other functional groups of the copolymer. In an exemplary embodiment, the matrix copolymer can be poly(L-lactide-co-glycolide) (PLGA). Increasing the content of GA can increase the degradation rate of the PLGA since GA is more hydrolytically active than LLA. The weight percent of the GA in the copolymer can be at least about 1%, 5%, 10%, 15%, 30%, 40%, 50%, or greater 50%.

As the literature data in Table 1 shows, the degradation time of PLGA decreases from three to four years to less than six months as the GA content increases from 0 wt % to 50 wt %. PLGA is amorphous throughout a wide range of GA content due to the disruption in the regularity in the polymer chain by the addition of another monomer. The decrease in degradation time is due both to the decreased crystallinity and increased hydrolytic activity of the GA.

Figure 7:
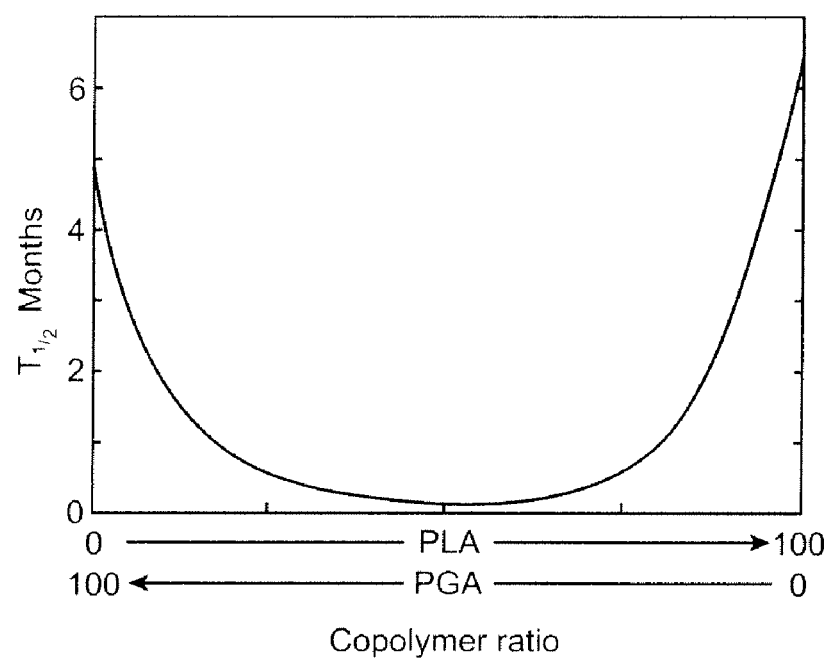
FIG. 7 shows the half-life of PLLA and PGA homopolymers and copolymers implanted in rat tissue.

Furthermore, as shown by FIG. 7, the relationship between the copolymer composition and the mechanical and degradation properties of the materials is not linear. FIG. 6 shows the half-life of PLLA and PGA homopolymers and copolymers implanted in rat tissue. Journal of Biomedical Materials Research, 11:711, 1977. The half-life in FIG. 6 refers to the amount of time for the modulus of a polymer to decrease by one half due to degradation of the polymer. For example, a copolymer of 50% GA and 50% LLA degrades faster than either homopolymer.

In some embodiments, the degradation time of the block copolymer composite can be reduced through the use of GA content in the matrix polymer. In other embodiments, the decrease in degradation time can be due both to GA content in the matrix polymer and the fast eroding elastomeric phase. In certain exemplary embodiments, the weight percent of GA and elastomeric content can be adjusted so that the degradation time of a stent scaffolding can be less than 18 months, 12 months, 8 months, 5 months, 3 months, or more narrowly, less than 3 months.

Additionally, the glassy blocks of the block polymer can be selected so that the glassy blocks are miscible with the matrix copolymer. In one embodiment, the glassy blocks can have the same composition as the matrix copolymer. In another embodiment, the glassy block can have a composition different from the matrix copolymer, but close enough so that the glassy block is miscible with the matrix polymer. In another embodiment, the glassy block can have composition different from the matrix polymer with the glassy blocks being miscible with the matrix copolymer. For example, some embodiments can include a PLLA matrix polymer and PLGA glassy blocks. Other embodiments can include a matrix polymer of PLGA and PLLA glassy blocks or PLGA glassy blocks.

Further embodiments include a composite including a block copolymer having glassy blocks that form all or part of the matrix or continuous phase. In such embodiments, the molecular weight is high enough such that the glassy blocks can make up a majority, a substantial portion, or all of the matrix or continuous phase. For example, embodiments of such "long" glassy blocks can make up more than 50, 70, 90, 95, or greater than 99 wt % of the continuous phase. The glassy blocks are substantially longer than the "short" elastomeric blocks described above. In certain embodiments, the molecular weight of the glassy blocks can be at least 2, 5, 8 10, or more than 10 times the molecular weight of the elastomeric blocks. In exemplary embodiments, the molecular weight of long glassy blocks can be 50-1,000 kg/mol, or greater than 1,000 kg/mol. In some embodiments, the matrix can be free of matrix polymers that are not a block of the block copolymer.

Figure 8A:
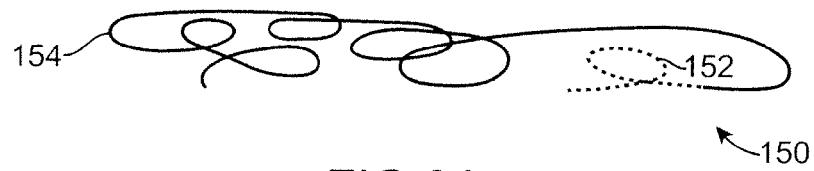
FIGS. 8A-E depict several embodiments of block copolymers having elastomeric blocks with long glassy blocks.

Several embodiments of block copolymers having elastomeric blocks with long glassy blocks are described herein. One embodiment includes a diblock copolymer containing long glassy blocks and short elastomeric blocks. FIG. 8A depicts a di-block copolymer 150 with a first end having an elastomeric block 152 (shown as a broken line) and a second end having a glassy block 154 (shown as a solid line).

Figure 8B:
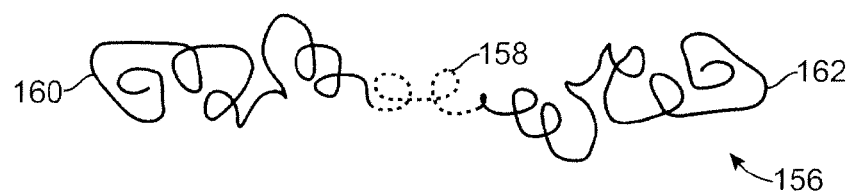
Figure 8C:
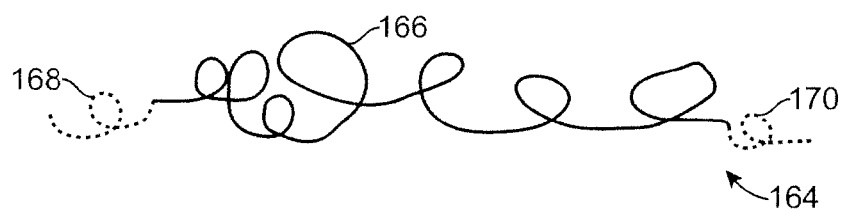

Another embodiment includes a triblock copolymer. A triblock copolymer can have an elastomeric block in the middle and long glassy blocks at two ends or a glassy block in the middle with elastomeric blocks at two ends. FIG. 8B depicts a tri-block copolymer 156 that has an elastomeric block 158 between long glassy blocks 160 and 162. FIG. 8C depicts a tri-block copolymer 164 with a glassy block 166 between elastomeric blocks 168 and 170.

Figure 8D:
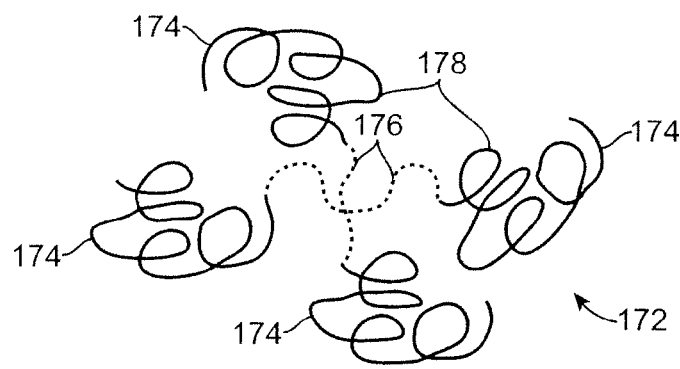
Figure 8E:
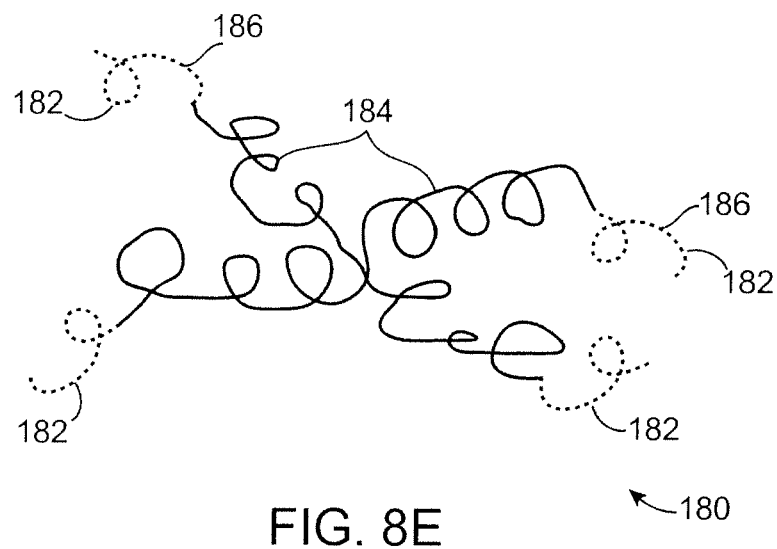

Additional embodiments include a star block copolymer having at least three arms. A star block copolymer can contain elastomeric blocks inside as a core and long glassy blocks outside as shell or long glassy blocks inside as a core and elastomeric blocks outside as a shell. FIG. 8D depicts a star block copolymer 172 having four arms 174. Arms 174 have inner segments 176 (shown as broken lines) and outer segments 178. Inner segments 176 are elastomeric blocks and outer segments 178 are long glassy blocks. FIG. 8E depicts a star block copolymer 180 having four arms 182. Arms 182 have inner segments 184 and outer segments 186. Inner segments 184 are long glassy blocks and outer segments 186 are elastomeric blocks.

Figure 9:
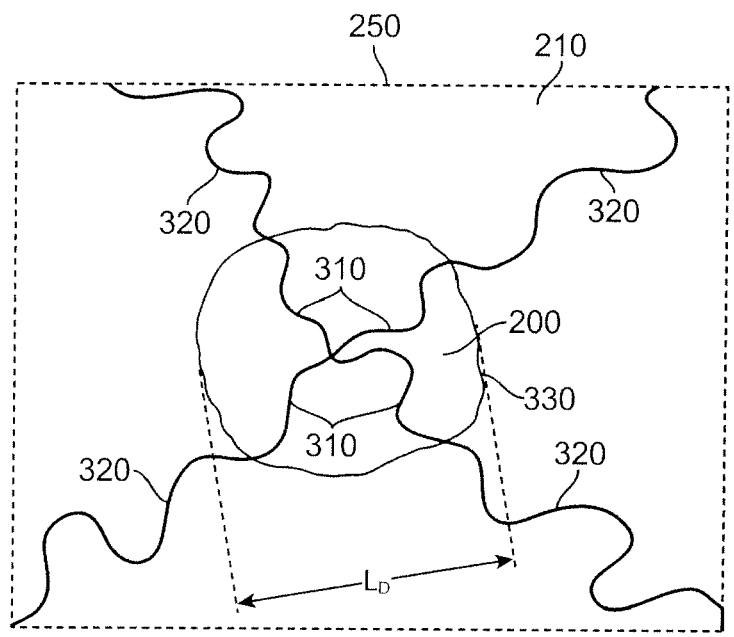
FIG. 9 depicts a schematic close-up view of a section of FIG. 3 of a discrete phase region and the interface between discrete phase region and a continuous phase.

FIG. 9 depicts a schematic close-up view of section 215 of FIG. 3 of a discrete phase region 200 and the interface between discrete phase region 200 and continuous phase 210. Section 215 includes a star block copolymer of FIG. 8D with inner segments 310 and outer segments 320. Line 330 delineates an approximate boundary between discrete phase region 200 and continuous phase 210. $L_D$ is a characteristic dimension of discrete phase region 200.

In some embodiments of a composite having a long glassy block, the elastomeric block can be a random or alternating copolymer. In such exemplary embodiments, the long PLLA glassy blocks can be bonded to elastomeric blocks including, but not limited to, P(GA-co-CL), P(GA-co-TMC), P(GA-co-CL-co-TMC), or P(CL-co-TMC). In exemplary embodiments, the polymeric material can include 1-30 wt %, or more narrowly, 2-20 wt % of the elastomeric blocks and about 80-98 wt % of the long glassy PLLA blocks.

In other embodiments, a composite can have a long glassy block with an elastomeric homopolymer. Exemplary diblock copolymers include PLLA-b-PDO, PLLA-b-PTMC and PLLA-b-PCL, with long glassy PLLA blocks being bonded to a short elastomeric block.

Exemplary triblock copolymers include PLLA-b-PDO-b-PLLA, PLLA-b-PCL-b-PLLA, with long glassy PLLA blocks at two ends and short elastomeric blocks in the middle.

Additional exemplary triblock copolymers include PDO-b-PLLA-b-PDO, PCL-b-PLLA-b-PCL, with long glassy PLLA blocks in the middle and short elastomeric blocks at two ends.

Exemplary star-block copolymers include PLLA-b-PDO and PLLA-b-PCL, with short, inner core elastomeric blocks and long glassy PLLA blocks as an outer shell. Alternatively, the star-block copolymer can have long glassy PLLA blocks as an inner core and short elastomeric blocks as an outer shell.

In further embodiments, the long glassy blocks of the block copolymer can be a random or alternating copolymer. In such embodiments, the long glassy blocks can be PLGA. As indicated above, the GA content increases the degradation rate of the composite which decreases the degradation time of a composite stent. The content of GA in the glassy blocks can be adjusted, alone or in combination with other parameters of the composite, so that the degradation time of a stent scaffolding can be less than 18 months, 12 months, 8 months, 5 months, 3 months, or more narrowly, less than 3 months.

In some embodiments, block polymers including glassy blocks and elastomeric blocks described herein can be formed by solution-based polymerization. In other embodiments, such block copolymers can be formed through melt phase polymerization. In solution-based polymerization, the reactive components involved in the polymerization reaction are dissolved in a solvent. The reaction scheme generally involves a step to form the elastomeric blocks and a step to form the glassy blocks. The elastomeric blocks can be formed first followed by formation of glassy blocks. Alternatively, the glassy blocks can be formed first.

The reactive components include monomers to form the elastomeric and glassy blocks, an initiator, and a catalyst. The reactive components are dissolved in a solvent at selected stages of the synthesis scheme to allow the polymerization to proceed. Following synthesis of the block copolymer, the block copolymer is precipitated from the reaction solution by pouring the solution into a nonsolvent of the block copolymer.

In one embodiment, the solvent for use in synthesizing the copolymer is devoid of alcohol functional groups. Such alcoholic groups may act as initiators for chain growth in the polymer. Solvents used to synthesize the block copolymer include, but are not limited to, chloroform, toluene, xylene, and cyclohexane. Initiators include, but are not limited to, pentaerythritol, dodecanol, ethanol, ethylene glycol, and polyethylene glycol. Catalysts used to facilitate the synthesis of the copolymer include, but are not limited to, stannous octoate, and stannous trifluoromethane sulfonate.

Embodiments of solution-based polymerization involve formation of a precursor block. The precursor block can either be the elastomeric block or the glassy block. Monomer units of the precursor block, a suitable initiator, and a suitable catalyst are added to a suitable solvent to form a polymerization solution. Suitable initiators, catalysts, and solvents are provided in the examples below, although the present invention is not limited to the initiators, catalysts, and solvents provided. The precursor block can act as a macro-initiator to initiate the polymerization of the second block. After the formation of the precursor block, monomer units of the second block and optionally catalyst are then added to the solution to form the block copolymer with elastomeric blocks and the glassy blocks. The solvent(s) for forming the second blocks can be selected so that the precursor block is soluble in the solvent(s) to enable the precursor blocks to copolymerize with the added monomer units of the second block.

In some embodiments, the elastomeric blocks are formed first in the synthesis of a diblock copolymer, a triblock copolymer with long glassy blocks at each end and an elastomeric block in the middle, and a star block copolymer with an inner core of elastomeric blocks and outer shell of long glassy blocks. In certain embodiments, the long glassy blocks are formed first in the synthesis of a triblock copolymer with elastomeric blocks at each end and a long glassy block in the middle, and a star block copolymer with an inner core of long glassy blocks and outer shell of elastomeric blocks.

In other embodiments, block copolymers can be formed by reacting a formed precursor copolymer swollen with a solvent that includes monomers of the second block. One of skill in the art can select a solvent that swells but does not dissolve the precursor polymer. The precursor block is swollen by a solvent after it is formed so that it can react with added monomers of the second block.

Embodiments of the composite disclosed herein may be formed into a polymer construct, such as a tube or sheet which can be rolled or bonded to form a tube. An implantable medical device can then be formed from the construct. For example, a stent can be fabricated from a tube by laser machining a pattern in to a tube. In another embodiment, a polymer construct may be formed from the composite mixture using an injection molding apparatus.

As indicated above, it is important for a stent to have high radial strength so that once it is deployed from the crimped state, it can support a lumen. In general, deforming a polymer construct can strengthen the polymer of the construct along an axis of deformation. In some embodiments of fabricating a stent from a polymer tube, the polymer tube can be radially expanded to increase the radial strength of the tube. The stent can then be fabricated from the polymer tube in its expanded state. Additionally, it has been observed that radially deforming a tube prior to cutting stent patterns increases the toughness of the stent scaffolding. In particular, the radial deformation reduces or eliminates cracks and breaking of the stent struts.

Representative examples of polymers that may be used to fabricate an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), poly-orthoester, polyanhydride, poly(glycolic acid), poly(glycolide), poly(L-lactic acid), poly(L-lactide), poly(D,L-lactic acid), poly(L-lactide-co-glycolide); poly(D,L-lactide), poly(caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially well suited for use in fabricating an implantable medical device according to the methods disclosed herein include ethylene vinyl alcohol copolymer (commonly known by the generic name EVOH or by the trade name EVAL), poly(butyl methacrylate), poly(vinylidene fluoride-co-hexafluoropropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

As indicated above, an implantable medical device such as a stent can be medicated by incorporating an active agent in a coating over the device or within the substrate of the device.

For the purposes of the present invention, the following terms and definitions apply:

"Molecular weight" can refer to the molecular weight of individual segments, blocks, or polymer chains. "Molecular weight" can also refer to weight average molecular weight or number average molecular weight of types of segments, blocks, or polymer chains.

The number average molecular weight (Mn) is the common, mean, average of the molecular weights of the individual segments, blocks, or polymer chains. It is determined by measuring the molecular weight of N polymer molecules, summing the weights, and dividing by N:

$$\overline{M}_n = \frac{\sum_i N_i M_i}{\sum_i N_i}$$

where Ni is the number of polymer molecules with molecular weight Mi. The weight average molecular weight is given by $$\overline{M}_w = \frac{\sum_i N_i M_i^2}{\sum_i N_i M_i}$$

where Ni is the number of molecules of molecular weight Mi.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

"Stress" refers to force per unit area, as in the force acting through a small area within a plane. Stress can be divided into components, normal and parallel to the plane, called normal stress and shear stress, respectively. True stress denotes the stress where force and area are measured at the same time. Conventional stress, as applied to tension and compression tests, is force divided by the original gauge length.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. For example, a material has both a tensile and a compressive modulus. A material with a relatively high modulus tends to be stiff or rigid. Conversely, a material with a relatively low modulus tends to be flexible. The modulus of a material depends on the molecular composition and structure, temperature of the material, amount of deformation, and the strain rate or rate of deformation. For example, below its Tg, a polymer tends to be brittle with a high modulus. As the temperature of a polymer is increased from below to above its Tg, its modulus decreases.

"Strain" refers to the amount of elongation or compression that occurs in a material at a given stress or load.

"Elongation" may be defined as the increase in length in a material which occurs when subjected to stress. It is typically expressed as a percentage of the original length.

Elongation to Break is the strain on a sample when it breaks. It is usually is expressed as a percent.

"Toughness" is the amount of energy absorbed prior to fracture, or equivalently, the amount of work required to fracture a material. One measure of toughness is the area under a stress-strain curve from zero strain to the strain at fracture. The stress is proportional to the tensile force on the material and the strain is proportional to its length. The area under the curve then is proportional to the integral of the force over the distance the polymer stretches before breaking. This integral is the work (energy) required to break the sample. The toughness is a measure of the energy a sample can absorb before it breaks. There is a difference between toughness and strength. A material that is strong, but not tough is said to be brittle. Brittle substances are strong, but cannot deform very much before breaking.

"Solvent" is defined as a substance capable of dissolving or dispersing one or more other substances or capable of at least partially dissolving or dispersing the substance(s) to form a uniformly dispersed solution at the molecular- or ionic-size level at a selected temperature and pressure. The solvent should be capable of dissolving at least 0.1 mg of the polymer in 1 ml of the solvent, and more narrowly 0.5 mg in 1 ml at the selected temperature and pressure, for example, ambient temperature and ambient pressure.

EXAMPLES

The examples and experimental data set forth below are for illustrative purposes only and are in no way meant to limit the invention. The following examples are given to aid in understanding the invention, but it is to be understood that the invention is not limited to the particular materials or procedures of examples. The Examples below are provided by way of illustration only and not by way of limitation. The parameters and data are not to be construed to limit the scope of the embodiments of the invention.

Example 1

Synthesis of PDO-b-PLLA Block Copolymer with Short PDO and PLLA Blocks

Figure 10:
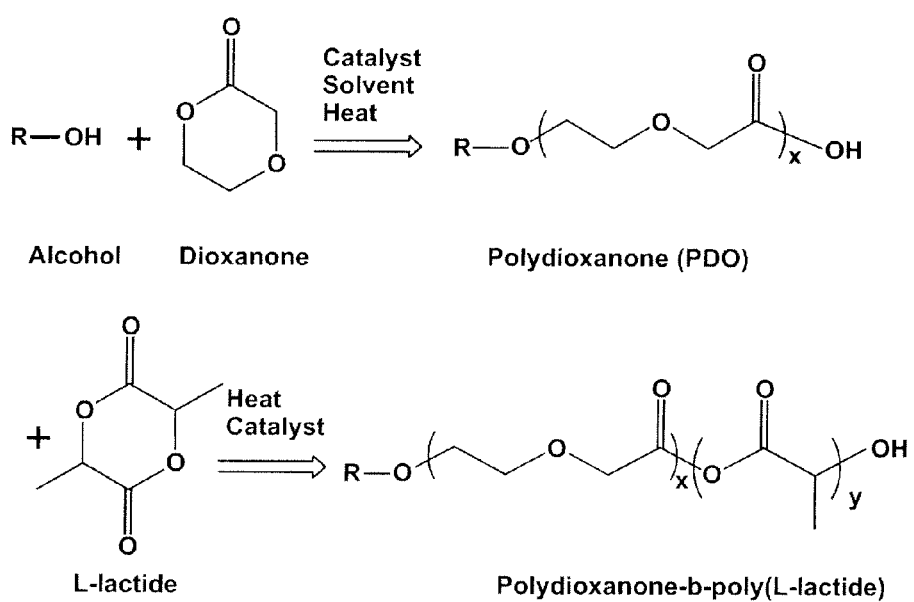
FIG. 10 depicts a synthetic route of PDO-b-PLLA block copolymer.

FIG. 10 depicts the synthetic route of PDO-b-PLLA block copolymer preparation. The copolymer is synthesized in two steps. In the first step, dioxanone (monomer), alcohol (initiator), catalyst and solvent are added into a reactor free of oxygen and moisture. Once the first PDO block is formed, LLA is added into reactor to form the PLLA block. The following describes a detailed polymerization process:

Step 1: One 500 mL three neck glassware reactor with a mechanical stirring rod is placed in a glove box which is filled with high purity nitrogen. The reactor is preheated to remove all moisture.

Step 2: 20 g dioxanone (DO) as monomer, 0.04 mL dodecanol as initiator, 70 mL toluene as solvent and 0.12 mL stannous octoate as catalyst are added into the reactor. The mixture is stirred at 100° C. for 48 hours.

Step 3: 10 g LLA monomer is then added into a reactor and the solution is stirred for another 48 hours.

Step 4: 100 mL CHCl$_3$ is then added into the reactor to dilute the final product. The product solution is then precipitated into 600 mL methanol, filtered out, and dried in vacuum at 80° C. until constant weight.

Another synthesis approach of the block copolymer synthesis the PLLA block with a hydroxyl end group first, and then use it as a macroinitiator to form the PDO block.

Examples 2, 3a-b, 4a-b illustrate synthesis of block copolymers with a long PLLA block and short fast eroding elastomeric homopolymer blocks

Example 2

Synthesis of PLLA-b-PDO Diblock Copolymer with Long PLLA Block and Short PDO Block (See FIG. 8A)

In Example 2, dodecanol as initiator, dioxanone (DO), and L-lactide (LLA) as monomers, and stannous octoate as catalyst are used.

Step 1: 40 g DO, 372 mg dodecanol, and 100 mL xylene are added into a reactor free of moisture and oxygen. All chemicals are mixed through mechanical stirring and the solution is heated to 110° C. Then 140 mg stannous octoate is added and the solution is stirred for 24 h to form a short PDO block.

Step 2: 200 g LLA, 300 mL xylene and 562 mg stannous octoate are added into the reactor to form a long PLLA block.

Step 3: Approximately 48 h later, the final product is precipitated into methanol, and dried in a vacuum oven at 90° C. for 48 h or till constant weight.

Example 3a

Synthesis of PLLA-b-PDO-b-PLLA Triblock Copolymer with Long PLLA Block at Two Ends and Short PDO Block in the Middle (See FIG. 8B)

In Examples 3a-b, ethylene glycol as initiator, DO and LLA as monomers, stannous octoate as catalyst, and xylene as solvent are used.

Step 1: 40 g DO, 124 mg ethylene glycol, and 100 mL xylene are added into a reactor free of moisture and oxygen. All chemicals are mixed through mechanical stirring and the solution is heated to 110° C. Then 140 mg stannous octoate is added and the solution is stirred at 110° C. for 24 h to form a short PDO block.

Step 2: 200 g LLA, 300 mL xylene and 562 mg stannous octoate are added into the reactor to form long PLLA block at two ends.

Step 3: Approximately 48 h later, the final product is precipitated into methanol, and dried in a vacuum oven at 90° C. for 48 h or till constant weight.

Example 3b

Synthesis of PDO-b-PLLA-b-PDO Triblock Copolymer with Long PLLA Block in the Middle and Short PDO Block at Two Ends (See FIG. 8C)

Step 1: 200 g LLA, 124 mg ethylene glycol, and 300 mL xylene are added into a reactor free of moisture and oxygen. All chemicals are mixed through mechanical stirring and the solution is heated to 110° C. Then 562 mg stannous octoate is added into the polymerization solution and the solution is stirred at 110° C. for 24 h to form a long PLLA chain.

Step 2: 40 g DO, 100 mL xylene, and 140 mg stannous octoate are added into the reactor to form a short PDO chain at two ends.

Step 3: Approximately 48 h later, the final product is precipitated into methanol, and dried in a vacuum oven at 90° C. for 48 h or till constant weight.

Example 4a

Synthesis of PDO-b-PLLA Star Block Copolymer with Short PDO Inner Core and Long PLLA Outer Shell (See FIG. 8D)

In Examples 4a-b, pentaerythritol as initiator, DO and LLA as monomers, stannous octoate as catalyst, and xylene as solvent are used.

Step 1: 20 g DO, 136 mg pentaerythritol, and 100 mL xylene are added into a reactor free of moisture and oxygen. All chemicals are mixed through mechanical stirring and the solution is heated to 110° C. Then 140 mg stannous octoate is added into the polymerization solution and the solution is stirred at 110° C. for 24 h to form short PDO chains.

Step 2: 200 g LLA, 300 mL xylene and 562 mg stannous octoate are then added into the reactor to form long PLLA chains.

Step 3: Approximately 48 h later, the final product is precipitated into methanol, and dried in a vacuum oven at 90° C. for 48 h or till constant weight.

Example 4b

Synthesis of PLLA-b-PDO Star-Copolymer with Long PLLA Inner Core and Short PDO Outer Shell (See FIG. 8E)

Step 1: 200 g LLA, 136 mg pentaerythritol, and 300 mL xylene are added into a reactor free of moisture and oxygen. All chemicals are mixed through mechanical stirring and the solution is heated to 110° C. Then 562 mg stannous octoate is added and the solution is stirred at 110° C. for 24 h to form long PLLA chains.

Step 2: 20 g DO, 100 mL xylene and 140 mg stannous octoate are then added into the reactor to form short PDO chains.

Step 3: Approximate 48 h later, the final product is precipitated into methanol, and dried in a vacuum oven at 90° C. for 48 h or till constant weight.

Examples 5a and 5b illustrate the synthesis of diblock copolymers with long PLGA blocks and an elastomeric block.

Example 5a

PLGA-b-PDO Diblock Copolymer Synthesis with Long PLGA Block and Short PDO Homopolymer Block (See FIG. 8A)

In Example 5a, dodecanol as initiator, dioxanone (DO), L-lactide (LLA), and glycolide (GA) as monomers, stannous octoate as catalyst are used.

Step 1: 40 g DO, 372 mg dodecanol, and 100 mL xylene are added into a reactor free of moisture and oxygen. All chemicals are mixed through mechanical stirring and the solution is heated to 110° C. Then 140 mg stannous octoate is added and the solution is stirred for 24 h to form a short PDO block.

Step 2: 180 g LLA, 20 g GA, 300 mL xylene and 562 mg stannous octoate are then added into the reactor to form a long PLGA block.

Step 3: Approximately 48 h later, the final product is precipitated into methanol, and dried in a vacuum oven at 90° C. for 48 h or till constant weight.

Example 5b

Synthesis of PLGA-b-P(GA-co-CL) Diblock Copolymer with Long PLGA Block and Short P(GA-co-CL) Random Block (See FIG. 8A)

In Example 5b, dodecanol as initiator, L-lactide (LLA), caprolactone (CL), and glycolide (GA) as monomers, stannous octoate as catalyst are used.

Step 1: 20 g CL, 20 g GA, 372 mg dodecanol and 100 mL xylene are added into a reactor free of moisture and oxygen. All chemicals are mixed through mechanical stirring and the solution is heated to 120° C. Then 140 mg stannous octoate is added and the solution is stirred for 48 h to form a short P(GA-co-CL) block.

Step 2: 180 g LLA, 20 g GA, 300 mL xylene and 562 mg stannous octoate are then added into the reactor to form a long PLGA block.

Step 3: Approximately 48 h later, the final product is precipitated into methanol, and dried in a vacuum oven at 90° C. for 48 h or till constant weight.

Examples 6a-c illustrate the synthesis of triblock copolymers with long PLGA blocks and an elastomeric block.

Example 6a

Synthesis of PLGA-b-PDO-b-PLGA Triblock Copolymer with Long PLGA Block at Two Ends and Short PDO Homo Block in the Middle (See FIG. 8B)

In Examples 6a-b, ethylene glycol as initiator, DO, LLA and GA as monomers, stannous octoate as catalyst, xylene as solvent are used.

Step 1: 40 g DO, 124 mg ethylene glycol and 100 mL xylene are added into a reactor free of moisture and oxygen. All chemicals are mixed through mechanical stirring and heated to 110° C. Then 140 mg stannous octoate is added and the solution is stirred at 110° C. for 24 h to form a short PDO block.

Step 2: 180 g LLA, 20 g GA, 300 mL xylene and 562 mg stannous octoate are added into the reactor to form long PLGA block at two ends.

Step 3: Approximately 48 h later, the final product is precipitated into methanol, and dried in a vacuum oven at 90° C. for 48 h or till constant weight.

Example 6b

Synthesis of PDO-b-PLGA-b-PDO Triblock Copolymer with Long PLGA Block in the Middle and Short PDO Block at Two Ends (See FIG. 8C)

Step 1: 180 g LLA, 20 g GA, 124 mg ethylene glycol, and 300 mL xylene are added into a reactor free of moisture and oxygen. All chemicals are mixed through mechanical stirring and the solution is heated to 110° C. Then 562 mg stannous octoate is added into the polymerization solution and the solution is stirred at 110° C. for 24 h to form a long PLGA chain.

Step 2: 40 g DO, 100 mL xylene, and 140 mg stannous octoate are added into the reactor to, form short PDO chain at two ends.

Step 3: Approximate 48 h later, the final product is precipitated into methanol, and dried in a vacuum oven at 90° C. for 48 h or till constant weight.

Example 6c

Synthesis of PLGA-b-P(GA-co-CL)b-PLGA Tri-block Copolymer with Long PLGA Block at Two Ends and Short P(GA-co-CL) Random Block in the Middle (See FIG. 8B)

In Example 6c, ethylene glycol as initiator, CL, GA and LLA as monomers, stannous octoate as catalyst, and xylene as solvent are used.

Step 1: 20 g CL, 20 g GA, 124 mg ethylene glycol and 100 ml, xylene are added into a reactor free of moisture and oxygen. All chemicals are mixed through mechanical stirring and the solution is heated to 120° C. Then 140 mg stannous octoate is added and the solution is stirred at 120° C. for 48 h to form a short P(GA-co-CL) block.

Step 2: 180 g LLA, 20 g GA, 300 mL xylene and 562 mg stannous octoate are added into the reactor to form a long PLGA block at two ends.

Step 3: Approximately 48 h later, the final product is precipitated into methanol, and dried in a vacuum oven at 90° C. for 48 h or till constant weight.

Examples 7a-c illustrate the synthesis of star block copolymers with long PLGA blocks and elastomeric blocks.

Example 7a

Synthesis of PDO-b-PLGA Star Block Copolymer with Short PDO Inner Core and Long PLGA Outer Shell (See FIG. 8D)

In Examples 7a-b, pentaerythritol as initiator, DO, LLA and GA as monomers, stannous octoate as catalyst, xylene as solvent are used.

Step 1: 40 g DO, 136 mg pentaerythritol, and 100 mL xylene are added into a reactor free of moisture and oxygen. All chemicals are mixed through mechanical stirring and the solution is heated to 110° C. Then 140 mg stannous octoate is added into the polymerization solution and the solution is stirred at 110° C. for 24 h to form short PDO chains.

Step 2: 180 g LLA, 20 g GA, 300 mL xylene and 562 mg stannous octoate are then added into the reactor to form long PLGA chains.

Step 3: Approximately 48 h later, the final product is precipitated into methanol, and dried in a vacuum oven at 90° C. for 48 h or till constant weight.

Example 7b

Synthesis of PLGA-b-PDO Star Block Copolymer with Long PLGA Inner Core and Short PDO Outer Shell (See FIG. 8E)

Step 1: 180 g LLA, 20 g GA, 136 mg pentaerythritol, and 300 mL xylene are added into a reactor free of moisture and oxygen. All chemicals are mixed through mechanical stirring and the solution is heated to 110° C. Then 562 mg stannous octoate is added and the solution is stirred at 110° C. for 24 h to form long PLGA chains.

Step 2: 40 g DO, 100 mL xylene and 140 mg stannous octoate are then added into the reactor to form short PDO chains.

Step 3: Approximately 48 h later, the final product is precipitated into methanol, and dried in a vacuum oven at 90° C. for 48 h or till constant weight.

Example 7c

Synthesis of P(GA-co-CL)-b-PLGA Star Block Copolymer with Short P(GA-co-CL) Inner Core and Long PLGA Outer Shell (FIG. 8D)

In Example 7c, pentaerythritol as initiator, CL, GA and LLA as monomers, stannous octoate as catalyst, and xylene as solvent are used.

Step 1: 20 g CL, 20 g GA, 136 mg pentaerythritol, and 100 mL xylene are added into a reactor free of moisture and oxygen. All chemicals are mixed through mechanical stirring and the solution is heated to 120° C. Then 140 mg stannous octoate is added into the polymerization solution and the solution is stirred at 120° C. for 48 h to form short P(GA-co-CL) chains.

Step 2: 180 g LLA, 20 g GA, 300 mL xylene and 562 mg stannous octoate are then added into the reactor to form long PLGA chains.

Step 3: Approximately 48 h later, the final product is precipitated into methanol, and dried in a vacuum oven at 90° C. for 48 h or till constant weight.

Example 9

Bioabsorbable Stent Preparation from the Block Copolymers Prepared in Examples 1-8

Step 1: Extrude tubing with designated inside diameter (ID) at 0.021 in and outside diameter (OD) at 0.64 in from the synthesized copolymer with long PLLA block and short fast eroding elastomeric homo/random block using a signal screw extruder at 200° C.

Step 2: Expand the extruded tubing to improve its mechanical properties along the axial and radial directions.

Step 3: Cut stents from expanded tubing using femto second laser and sterilize all stents after crimping.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent body fabricated from a polymer composite including a biodegradable elastomeric phase dispersed within a biodegradable polymeric matrix, the composite comprising:
   a block copolymer comprising an elastomeric homopolymer block and a glassy polymer block, wherein the elastomeric phase comprises the elastomeric homopolymer block and the matrix comprises the glassy polymer block, wherein the elastomeric block is tougher than the glassy polymer block and the polymeric matrix at physiological conditions
   wherein the polymeric matrix further comprises a glassy matrix polymer, the glassy matrix polymer being blended with the block copolymer, wherein the glassy polymer block is miscible with the glassy matrix polymer, wherein a majority of the elastomeric phase further comprises an elastomeric homopolymer the same as the elastomeric homopolymer block, and wherein the polymer composite is 5-30 wt % of the elastomeric homopolymer and 0.5-5 wt % of the block copolymer, wherein the glassy matrix polymer is poly(L-lactide), the elastomeric homopolymer is polydioxanone, and the block copolymer is poly(L-lactide)-b-poly(L-lactide)-co-polydioxanone.

* * * * *